(12) United States Patent
Eisenbrey et al.

(10) Patent No.: US 11,305,013 B2
(45) Date of Patent: Apr. 19, 2022

(54) SURFACTANT MICROBUBBLES AND PROCESS FOR PREPARING AND METHODS OF USING THE SAME

(71) Applicants: Drexel University, Philadelphia, PA (US); Thomas Jefferson University, Philadelphia, PA (US)

(72) Inventors: John Robert Eisenbrey, Philadelphia, PA (US); Margaret Alison Wheatley, Media, PA (US); Patrick O'Kane, Philadelphia, PA (US); Lorenzo Albala, Philadelphia, PA (US); Flemming Forsberg, Lafayette Hill, PA (US)

(73) Assignees: Drexel University, Philadelphia, PA (US); Thomas Jefferson University, Philadelphia, PA (US)

( * ) Notice: Subject to any disclaimer, the term of this patent is extended or adjusted under 35 U.S.C. 154(b) by 811 days.

(21) Appl. No.: 14/835,636

(22) Filed: Aug. 25, 2015

(65) Prior Publication Data
US 2016/0059036 A1    Mar. 3, 2016

Related U.S. Application Data

(60) Provisional application No. 62/042,184, filed on Aug. 26, 2014.

(51) Int. Cl.
| | |
|---|---|
| *A61K 41/00* | (2020.01) |
| *A61K 49/22* | (2006.01) |
| *A61K 33/00* | (2006.01) |
| *A61K 9/00* | (2006.01) |
| *A61N 5/10* | (2006.01) |

(52) U.S. Cl.
CPC ........ *A61K 41/0028* (2013.01); *A61K 9/0009* (2013.01); *A61K 33/00* (2013.01); *A61K 41/0038* (2013.01); *A61K 49/223* (2013.01); *A61N 2005/1098* (2013.01)

(58) Field of Classification Search
CPC ...... A61N 5/10; A61K 9/5015; A61K 49/223; A61K 41/0028
See application file for complete search history.

(56) References Cited

U.S. PATENT DOCUMENTS

| | | | | |
|---|---|---|---|---|
| 5,487,390 | A | * | 1/1996 | Cohen ................. A61K 9/1271 424/501 |
| 6,139,819 | A | | 10/2000 | Unger et al. |
| 2004/0013662 | A1 | * | 1/2004 | Porter .................... A61P 29/00 424/94.61 |
| 2004/0258760 | A1 | | 12/2004 | Wheatley et al. |
| 2004/0258761 | A1 | | 12/2004 | Wheatley et al. |
| 2008/0247957 | A1 | | 10/2008 | Wheatley |
| 2008/0279783 | A1 | | 11/2008 | Wheatley et al. |
| 2009/0196827 | A1 | | 8/2009 | Wheatley et al. |
| 2012/0109045 | A1 | | 5/2012 | Wrenn et al. |

OTHER PUBLICATIONS

Kwan et al. (Theranostics, 2012, 2(12), p. 1174-1184). (Year: 2012).*
Kheir et al., Science Translational Medicine, 2012, vol. 4, Issue 140, pp. 140-188. (Year: 2012).*
Albala, L., et al., Apr. 10, 2014, "Indirect Plasma Sterilization of Ultrasound Contrast Agent", in "Drexel University Research Day 2014".
Albala, L., et al., Jun. 16, 2014, "Indirect Plasma Sterilization of Ultrasound Contrast Agent", in "2014 International Symposium on Molecular Medicine and Infectious Disease" 41.
Brown J. M., et al., 2004, "Exploiting Tumour Hypoxia In Cancer Treatment", Nature Reviews, Cancer, 4, 437-447.
Chen, Q., et al., 2002, "Improvement of Tumor Response by Manipulation of Tumor Oxygenation During Photodynamic Therapy", Photochemistry and Photobiology, 76(2), 197-203.
Erler, J. T., et al., 2004, "Hypoxia-Mediated Down-Regulation of Bid and Bax in Tumors Occurs via Hypoxia-Inducible Factor 1-Dependent and -Independent Mechanisms and Contributes to Drug Resistance", Molecular and Cellular Biology, 24(7), 2875-2889.
Kunugita, N., et al., 2001, "Radiotherapy after hyperbaric oxygenation improves radioresponse in experimental tumor models", Cancer Letters, 164, 149-154.
Liao, D., et al., 2007, "Hypoxia: A key regulator of angiogenesis in cancer", Cancer Metastasis Rev., 26, 281-290.
Moeller, B. J., et al., 2004, Radiation activates HIF-1 to regulate vascular radiosensitivity in tumors: Role of reoxygenation, free radicals, and stress granules, Cancer Cell, 5, 429-441.
Unruh, A., et al., 2003, "The hypoxia-inducible factor-1 alpha is a negative factor for tumor therapy", Oncogene, 22, 3213-3220.
Vaupel, P., 2004, "Tumor Microenvironmental Physiology and Its Implications for Radiation Oncology", Seminars in Radiation Oncology, 14(3), 198-206.
Xu, R., et al., 2005, "Inhibition of Glycolysis in Cancer Cells: A Novel Strategy to Overcome Drug Resistance Associated with Mitochondrial Respiratory Defect and Hypoxia", Cancer Res , 65(2), 613-621.
Albala, L., Mar. 2014, "Indirect Plasma Sterilization of Ultrasound Contrast Agent", Master's Thesis, Drexel University.
Eisenbrey, J. E., et al., "Development of an ultrasound sensitive oxygen carrier for oxygen delivery to hypoxic tissue", Int J Pharm. 478(1), Jan. 15, 2015, 361-367.

* cited by examiner

*Primary Examiner* — Michael G. Hartley
*Assistant Examiner* — Leah H Schlientz
(74) *Attorney, Agent, or Firm* — Saul Ewing Arnstein & Lehr LLP; Kathryn Doyle; Brian R. Landry (57) ABSTRACT

The invention relates to an ultrasound contrast agent (UCA) comprising an outer shell and a gas core. The gas core is filled with oxygen, and the outer shell comprises a first surfactant and a second surfactant. The invention also relates to a method of making an oxygen-filled UCA and delivering oxygen to a local area of a subject's body. The method comprises injecting a composition comprising an oxygen-filled UCA of the invention into the subject's body; directing ultrasound radiation to the local area in an intensity sufficient to rupture the UCA.

12 Claims, 11 Drawing Sheets

SURFACTANT MICROBUBBLES AND PROCESS FOR PREPARING AND METHODS OF USING THE SAME

CROSS-REFERENCE TO RELATED APPLICATIONS

This application claims priority under 35 U.S.C. § 119(e) to U.S. Provisional Patent Application No. 62/042,184, filed Aug. 26, 2014, the entire contents of which is hereby incorporated by reference.

STATEMENT REGARDING FEDERALLY SPONSORED RESEARCH OR DEVELOPMENT

This invention was made with government support under grant number W81XWH-11-1-0630 awarded by United States Army Medical Research & Material Command and grant number CA190926 awarded by the National Institutes of Health. The government has certain rights in the invention.

BACKGROUND OF THE INVENTION

The highly chaotic process of tumor angiogenesis (whereby cancerous tumors recruit and develop new blood vessels) results in hypoxic conditions on the cellular level, because oxygen transport within the tumor is inadequate to compensate for the high metabolic rate. Whereas healthy subcutaneous tissue generally exhibits oxygen partial pressures from 40-60 mmHg, many cancers exhibit partial pressures between 2 and 18 mmHg. Hypoxic cells have been shown to be more resistant to death from radiation exposure than aerobic cells. This phenomenon provides an innate level of tumor resistance to radiotherapy and chemotherapy, resulting in decreased tumor response and increased rates of recurrence. Systemic approaches for oxygen ($O_2$) delivery using hyperbaric chambers for overcoming tumor hypoxia have shown some promise, but this becomes technically challenging in conjunction with radiation therapy from a temporal standpoint and localized changes in oxygenation levels have been modest.

SUMMARY OF THE INVENTION

In one aspect, the invention relates to an ultrasound contrast agent (UCA) comprising an outer shell and a gas core. The gas core is filled with oxygen, and the outer shell comprises a first surfactant and a second surfactant. The purity of the oxygen enclosed in the UCA is in the range of about 22% to about 100%. The first surfactant is d-α-tocopheryl polyethylene glycol 1000 succinate (TPGS) or polyoxyethylene sorbitan monooleate, while the second surfactant is selected from the group consisting of: sorbitan esters, alkylphenol ethoxylate-based surfactants, alcohol ethoxylate-based surfactants, silicone-based surfactants, alkyl poly(ethylene oxide), alkylphenol poly(ethylene oxide), copolymers of poly(ethylene oxide) and polypropylene oxide), alkyl polyglucosides, fatty alcohols, cocamide MEA, cocamide DEA, and polysorbates. The mean diameter of the UCA is in the range of 1 μm to 10 μm. The half-life of the UCA under 5 MHz ultrasound is in the range of 1 to 20 minutes.

In another aspect, the invention relates to a method of making an oxygen-filled UCA. The method comprises the steps of: mixing a first surfactant and a second surfactant in phosphate buffered saline; heating the mixture until both surfactants are dissolved; cooling said mixture to room temperature while stirring; optionally autoclaving the mixture and cooling the mixture while stirring; placing the vessel containing the mixture in an ice bath, purging said mixture using a gas while sonicating said mixture; separating microbubbles; adding a lyoprotectant to the microbubbles; freeze-drying the microbubbles; sealing the microbubbles under vacuum; and refilling the microbubbles with substantially pure oxygen.

In yet another aspect, the invention relates to a method of delivering oxygen to a local area of a subject's body. The method comprises injecting a composition comprising a UCA of the invention into the subject's body; and directing ultrasound radiation to the local area in an intensity sufficient to rupture the UCA.

In yet another aspect, the invention relates to a method of improving effectiveness of radiotherapy and chemotherapy against cancer. The method comprises the steps of: injecting a composition comprising a UCA of the invention into a subject suffering from cancer; directing ultrasound radiation to a location of said cancer in an intensity sufficient to rupture the UCA; and applying radiotherapy and/or chemotherapy.

In yet another aspect, the invention relates to a method of delivering a drug to a subject. The method comprises the steps of: preparing a drug-containing UCA; injecting the UCA into the circulatory system of the subject; and directing ultrasound radiation to a location of interest with an intensity sufficient to rupture the drug-containing UCA.

In yet another aspect, the invention relates to a method of improve the effectiveness of a therapeutic agent. The method comprises the steps of: preparing an oxygen-filled UCA; co-injecting the UCA with the therapeutic agent into the circulatory system of the subject; and directing ultrasound radiation to a location of interest with an intensity sufficient to rupture the oxygen-filled UCA.

BRIEF DESCRIPTION OF THE DRAWINGS

For the purpose of illustrating the invention, there are certain embodiments of the invention depicted in the drawings. However, the invention is not limited to the precise arrangements and instrumentalities of the embodiments depicted in the drawings.

FIGS. 8A-8E depict in vivo images showing enhancement of the renal vasculature in a 3 kg swine after injection of SE61 filled with $O_2$. Imaging was performed using a SIEMENS® S3000 ultrasound system with 9 MHz linear probe in CPS mode. Microbubble signal is displayed in the left half of each images, while the normal B-mode ultrasound is displayed in the right half of each image. FIGS. 8A, 8B, 8C, 8D, and 8E were taken at 19, 26, 34, 44, and 54 seconds after injection, respectively. These data demonstrate the stability of the oxygen filled microbubble and ability to deliver oxygen in a large animal model.

DEFINITIONS

As used herein, each of the following terms has the meaning associated with it in this section.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used herein, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

As used herein, "half-life" refers to the amount of time required for half of microbubbles ruptured under specific condition.

As used herein, "lyoprotectant" and "cryoprotectant" are interchangeable. Both refer to a compound that minimizes or prevents structural and/or functional integrity loss of UCA that can occur during the drying stage of a freeze-drying process.

As used herein, the term "substantially pure" refers to a gas having a purity more than 80% weight percentage.

As used herein, the term "hydrophilic-lipophilic balance" ("HLB") is a relative measure of the ratio of polar and non-polar groups present in a surfactant.

As used herein, the term "microbubble" is used interchangeably with "ultrasound contrast agent", which is defined below.

As used herein, the term "SPAN®" refers to a sorbitan monoester that is used as a non-ionic detergent, and sold by Sigma-Aldrich.

As used herein, "ultrasound contrast agent" ("UCA") refers to surfactant-stabilized gas bubbles.

DETAILED DESCRIPTION OF THE INVENTION

One aspect of the present invention relates to a gas delivery method utilizing an ultrasound contrast agent (UCA) to deliver a gas to a location of a subject's body. The gas can be air, nitrogen, oxygen, nitric oxide, perfluorocarbon, sulfur hexafluoride, carbon dioxide and the like. In one aspect, the gas delivery method comprises: preparing a UCA with a gas core filled with a specific gas; injecting the UCA into a subject's body; and directing ultrasound radiation to a specific location of the subject's body with an intensity sufficient to rupture the UCA. Thus, the gas inside the UCA will be released to the local tissue of the subject. The invention also includes a UCA suitable for use in the gas delivery method, a method of making, and a method of using the same. Another aspect of the invention includes a method of sterilization and a method of making a sterilized UCA are included in the invention.

Composition

Figure 5:
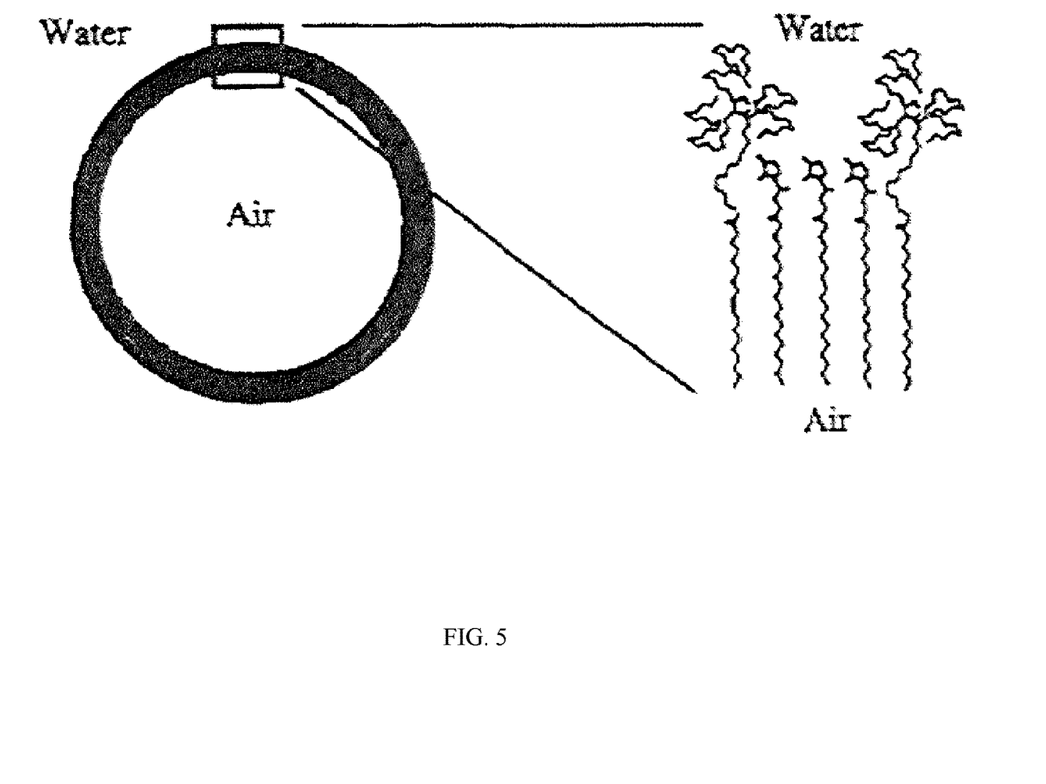
FIG. 5 depicts a schematic diagram of an ultrasound contrast agent (UCA) composition. The core of a UCA can be any gas, air, a drug, or a mixture of drugs.

In one aspect, the invention includes a UCA comprising an outer shell and a gas core filled with substantially pure gas (FIG. 5). The gas bubble can be stabilized by at least two surfactants.

In one embodiment, the gas is oxygen. Cancer cells living in hypoxic conditions are resistant to radiation exposure. Therefore, delivering oxygen to cancer cells using the gas delivery method in the invention can improve effectiveness of radiotherapy and chemotherapy.

In another embodiment, the gas is nitrogen. In yet another embodiment, the gas is nitric oxide. In yet another embodiment, the gas is a mixture of nitric oxide and oxygen. Nitric oxide/oxygen blends promote capillary and pulmonary dilation to treat primary pulmonary hypertension in neonatal patients.

In certain embodiments, the purity of oxygen by volume can be about 100%, or at least about 95%, or at least about 90%, or at least about 85%, or at least about 80%, or at least 22%.

Surfactants useful in the practice of the invention can include any biocompatible surfactants known in the art including anionic, cationic, zwitterionic, and non-ionic surfactants. In an embodiment, the UCA comprises two non-ionic surfactants. When the surfactant is non-ionic, the hydrophilic-lipophilic balance (HLB) of the surfactant is between about 6 and about 16. Non-limiting examples of non-ionic surfactants useful in the practice of the invention include, but are not limited to, d-α-tocopheryl polyethylene glycol 1000 succinate (TPGS), sorbitan esters, alkylphenol ethoxylate-based surfactants, alcohol ethoxylate-based surfactants, silicone-based surfactants, alkyl poly(ethylene oxide), alkylphenol poly(ethylene oxide), copolymers of poly(ethylene oxide) and polypropylene oxide), alkyl polyglucosides, fatty alcohols, cocamide MEA, cocamide DEA, and polysorbates.

In certain embodiments, the two non-ionic surfactants are selected from the group consisting of sorbitan esters, polysorbates and TPGS. The possible compositions in these embodiments include combinations of sorbitan esters/polysorbates, sorbitan esters/TPGS and polysorbates/TPGS. The different surfactants in various combinations, in various concentrations, and encapsulating different gases will dictate the packing density and strength of inter-molecular forces around the gas.

In another embodiment, the first surfactant is TPGS, and the second surfactant is sorbitan esters. In yet another embodiment, the first surfactant is polyoxyethylenesorbitan monolaurate, and the second surfactant is sorbitan esters.

UCA Size

The UCA in the examples can have a mean diameter in the range of 1 µm to about 10 µm. In certain embodiments, the UCA in the invention has a mean diameter in range of 2 µm to 7 µm, 2 µm to 6 µm, or 2 µm to 5 µm. In one instance, the UCA in the invention has mean diameter of about 3 µm. Although the examples discuss microbubbles only, it is well understood that nanobubbles with a mean diameter between 1 nanometer and 1,000 nanometers are included in this invention. Mechanistically, nanobubbles and microbubbles function in the same way in terms of delivering gas.

UCA Stability and Functionality

A shelf-stable UCA is preferred for the gas delivery method, as the UCA has to be stable long enough to pass through the circulatory system and potentially to the tumor vasculature. In certain embodiments, the UCA comprises surfactants and a particulate material. In one embodiment, the particulate material is one of the surfactants. In other embodiments, an exogenous particulate material in incorporated into the UCA. The exogenous particulate material is incorporated any time prior to the sonication step. Examples of particles that are useful in the practice of the invention include, but are not limited to: solid surfactant; quantum dots; colloidal gold; carbon nanotubes; carbon nanotubes containing drug; polystyrene; SPIO (superparamagnetic iron oxide); iron oxide; coated nanoparticles containing a drug; imaging agents such as gas; radiopaque species; MRI contrast agents such as Gadolinium compounds; a drug in nanoparticle form (e.g., by grinding); nanocapsules; hollow drug-containing contrast medium containing particles with attached targeting agents such as antibodies, portions of antibodies, peptide sequences etc.; viruses; and inactivated viruses.

To test the stability of a UCA, ultrasound radiation under certain intensity is applied to the UCA. In one embodiment, the half-life of the UCA under 0.69 MPa ultrasound is in the range of 1 to 20 minutes. In certain embodiments, the half-life of the UCA under 0.69 MPa ultrasound is in the range of 5 to 20 minutes; or in the range of 10 to 20 minutes. In one instance, the half-life of the UCA under 0.69 MPa ultrasound is about 15 minutes.

Method of Making a UCA

In another aspect, the invention includes a method of making a UCA. The general steps are the following:
a. mixing a first surfactant and a second surfactant in phosphate buffered saline;
b. heating the mixture until both surfactants are dissolved;
c. cooling said mixture to room temperature while stirring;
d. optionally autoclaving the mixture and cooling the mixture while stirring;
e. placing the mixture in a vessel in an ice bath, purging said mixture using a first gas while sonicating said mixture;
f. separating microbubbles;
g. adding a lyoprotectant to the microbubbles;
h. freeze-drying the microbubbles;
i. sealing the microbubbles under vacuum; and
j. refilling the microbubbles with a second gas.

In one embodiment, the lyoprotectant is a saccharide added prior to freeze-drying the UCA. In one embodiment, the saccharide is trehalose; in another embodiment, the saccharide is glucose. In a non-limiting exemplary example, a UCA is diluted in 1:1 by volume with a solution of the saccharide. The final concentration of the saccharide in the mixture with the UCA can be from about 1 millimolar (mM) to less than about 200 mM, preferably from about 10 mM to about 140 mM, and more preferably about 50 mM to about 100 mM. The mixture is then flash frozen, for instance, in liquid nitrogen, and then freeze-dried at a temperature of about −80° C. to about −70° C. In one embodiment, octafluoropropane gas is the first gas to purge the mixture to form bubbles having octafluoropropane gas.

The method described herein can be used to reconstitute a UCA with any gas of choice, including, but not limited to, oxygen, nitrogen, or nitric oxide. An exemplary method of freeze drying and filling UCA with gas is as follows. An aliquot of a UCA suspension is placed in a 15 ml lyophilization vial (West Pharmaceutical Services, Lionville, Pa.). A FLUROTEC® lyophilization stopper (West Pharmaceutical Services) is placed in the neck of the vial up to the first groove. The agent is then flash frozen in liquid nitrogen. The vial is placed on a previously chilled (initially to −80° C.) two-shelf stoppering rack of a VIRTIS® Benchtop freeze-dryer (Gardiner, N.Y.) and freeze dried at pressures below 300 µBar and a condenser temperature of −76° C. For gas filling, the piston of the stoppering rack is lowered prior to venting the freeze dryer, thus sealing the stopper in the vial under vacuum. The stoppered vial is removed from the freeze dryer, and the gas of choice is introduced into the individual vial from a tank, passing through a sterile filter, via a needle pierced through the stopper septum. A gas flow rate of 50 ml/min for the first 5 to 10 seconds and then 20 ml/min for the next minute can be used to insure the vial is filled. For capsules filled with air, the freeze drier is vented to the atmosphere prior to stoppering the vials.

In one embodiment, oxygen is used to charge a UCA to generate an oxygen-filled UCA. In certain embodiments, the purity of oxygen is about 100%, or at least about 95%, or at least about 90%, or at least about 85%, or at least about 80%.

In certain embodiments, the gas-filled UCA is reconstituted before use by addition of an aqueous solution. In one embodiment, the aqueous solution is sterile water. In another embodiment, the aqueous solution is phosphate buffered saline.

In Vitro Oxygen Release

Figure 4:
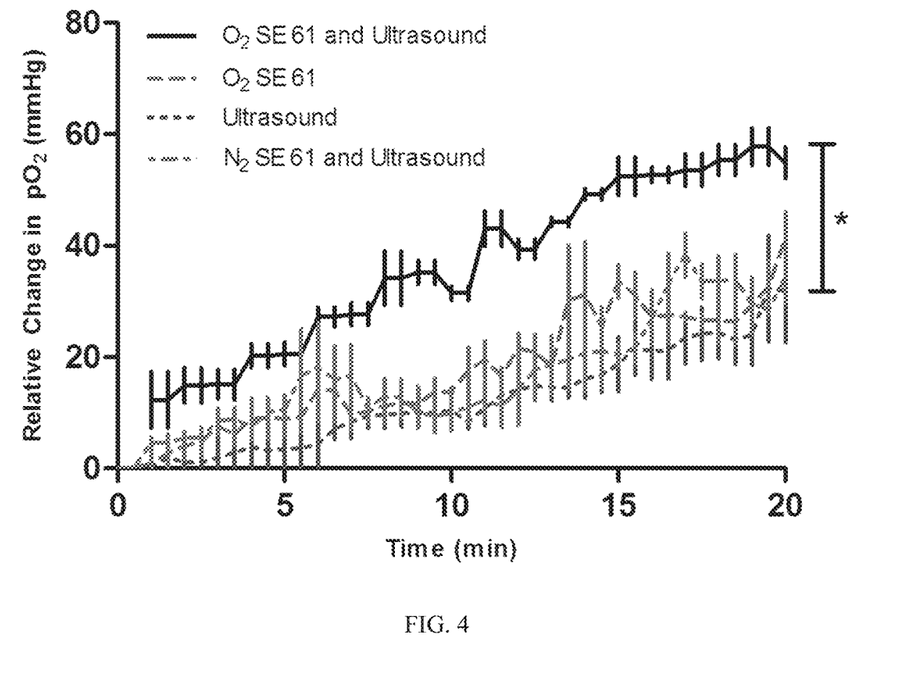
FIG. 4 depicts relative change in oxygen partial pressure ($pO_2$) levels in 100 ml of degassed saline over 20 minutes under different conditions: $SE61_{O2}$ and ultrasound, ultrasound alone, $SE61_{O2}$ alone, and nitrogen filled SE61 with ultrasound (*$p<0.0001$).

An oxygen-filled UCA made according to the methods described herein was confirmed to rupture and release oxygen under ultrasound radiation. Ultrasound triggering was performed using a SONIXRP® scanner with a PA4-2 cardiac probe operating at 100% acoustic output (approximately 3.6 MPa peak-peak pressure) at 4 MHz in power Doppler mode. Two milliliters of UCA was added to 100 ml of degassed saline. Samples were triggered with ultrasound over 20 minutes with readings obtained every 30 seconds. FIG. 4 shows that triggered UCAs release oxygen.

In Vivo Application

Figure 6:
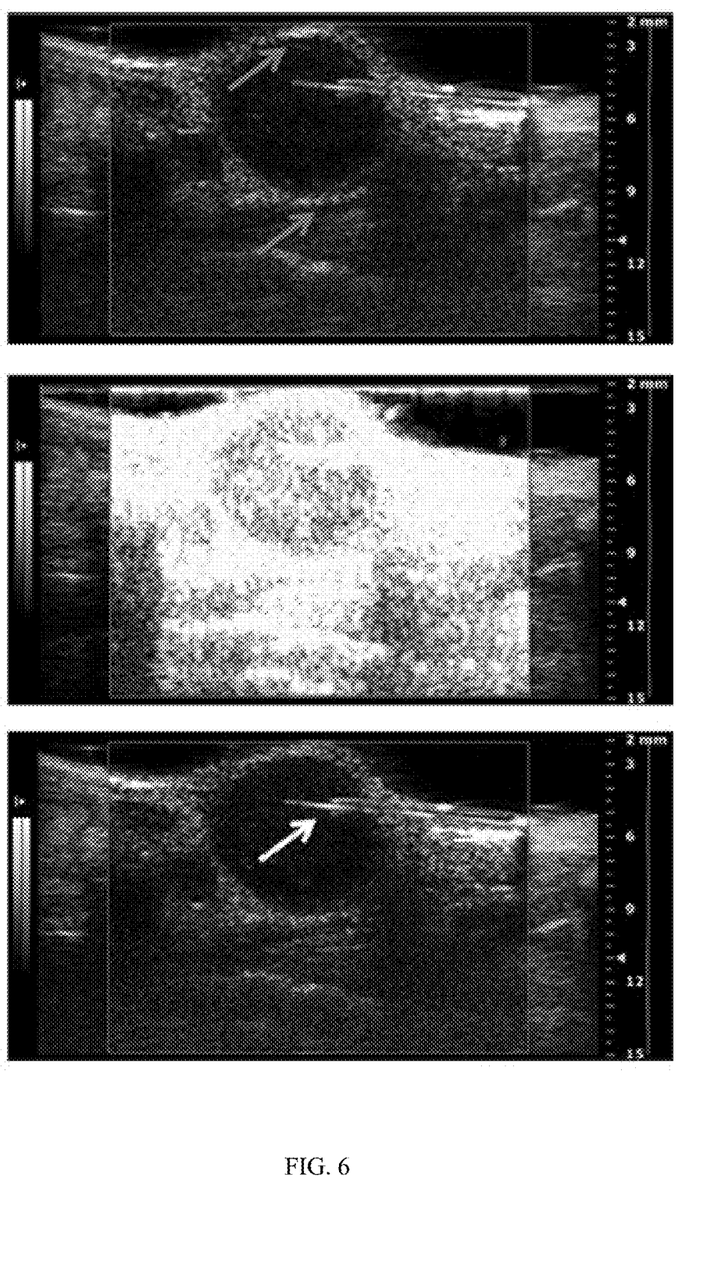
FIG. 6 depicts in vivo proof of concept delivery experiments. The top ultrasound image shows contrast $pO_2$ probe arrival within the periphery of the tumor with slight peripheral enhancement denoted with two arrows. The middle ultrasound image shows flash-destructive ultrasound pulse used to destroy the microbubbles. The bottom ultrasound image shows a slight decrease in peripheral enhancement immediately after microbubble destruction.
Figure 7:
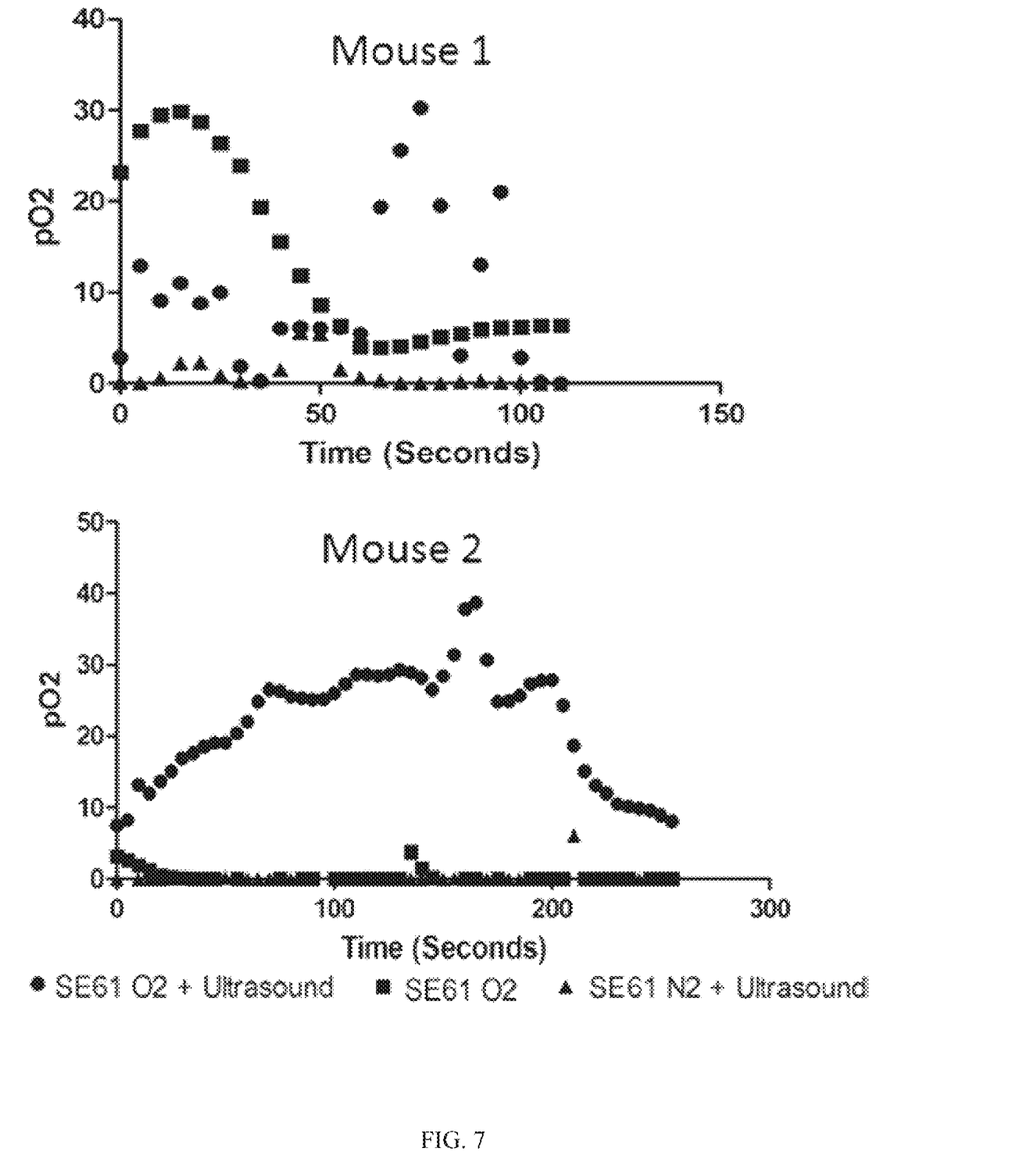
FIG. 7 depicts the intra-tumoral pO2 levels over time for Mouse 1 and Mouse 2 after injection of $SE61_{O2}$ with ultrasound, $SE61_{O2}$ alone, and $SE61_{N2}$ with ultrasound.
Figure 8A:
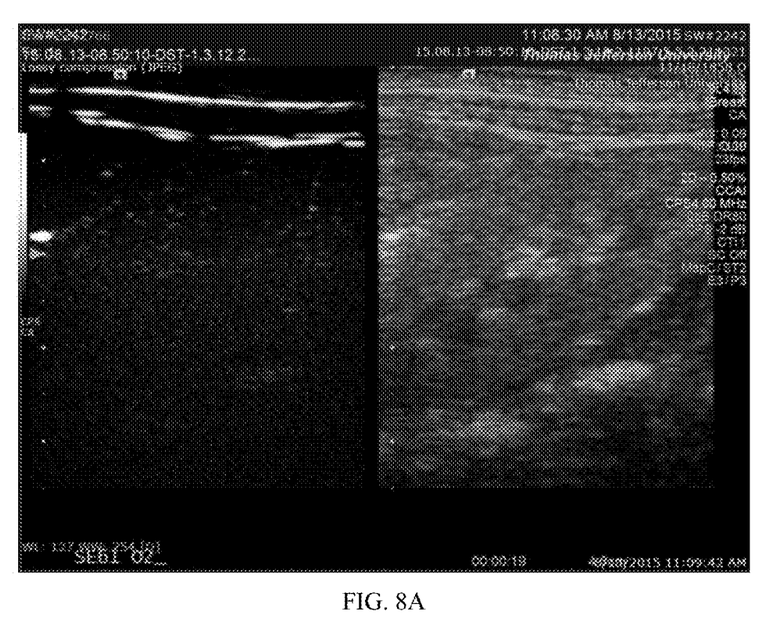
Figure 8B:
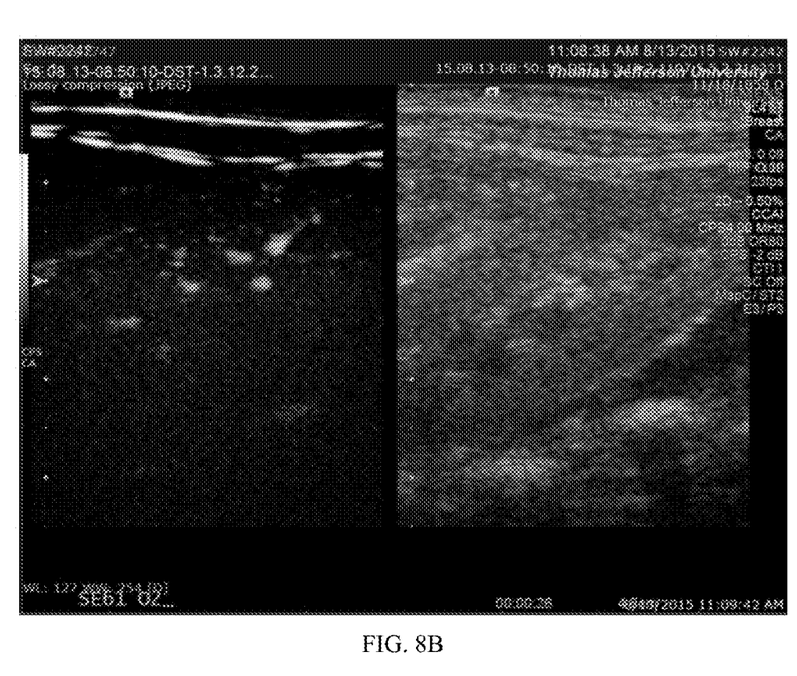
Figure 8C:
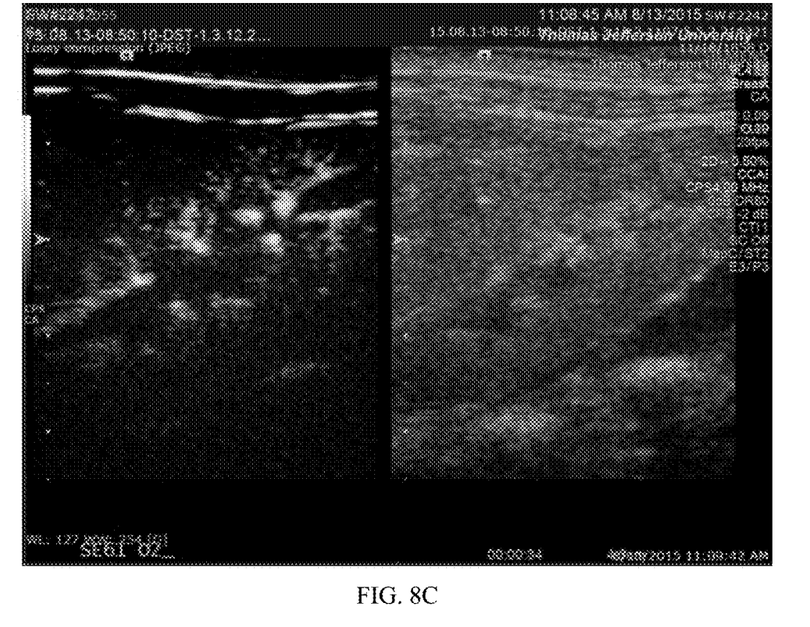
Figure 8D:
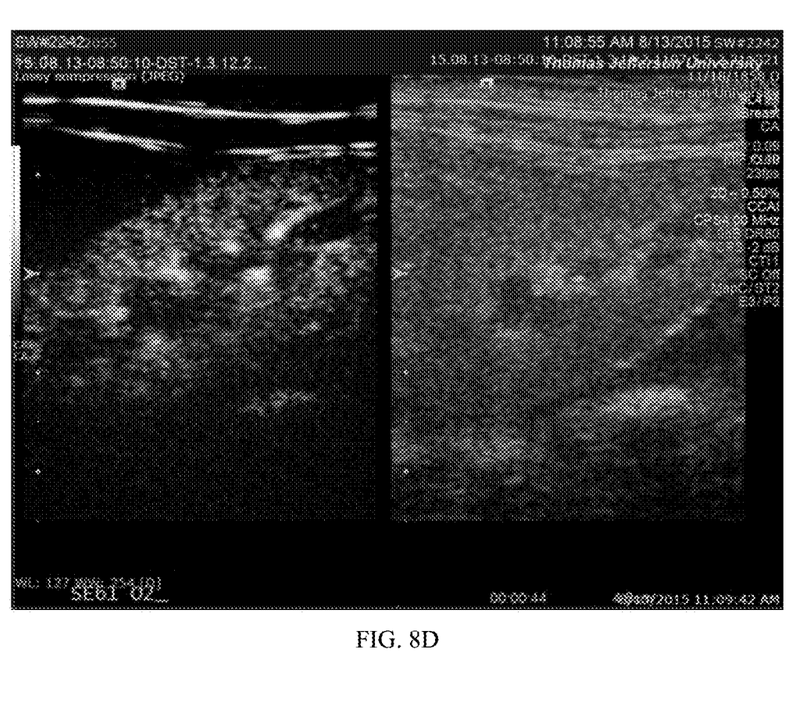
Figure 8E:
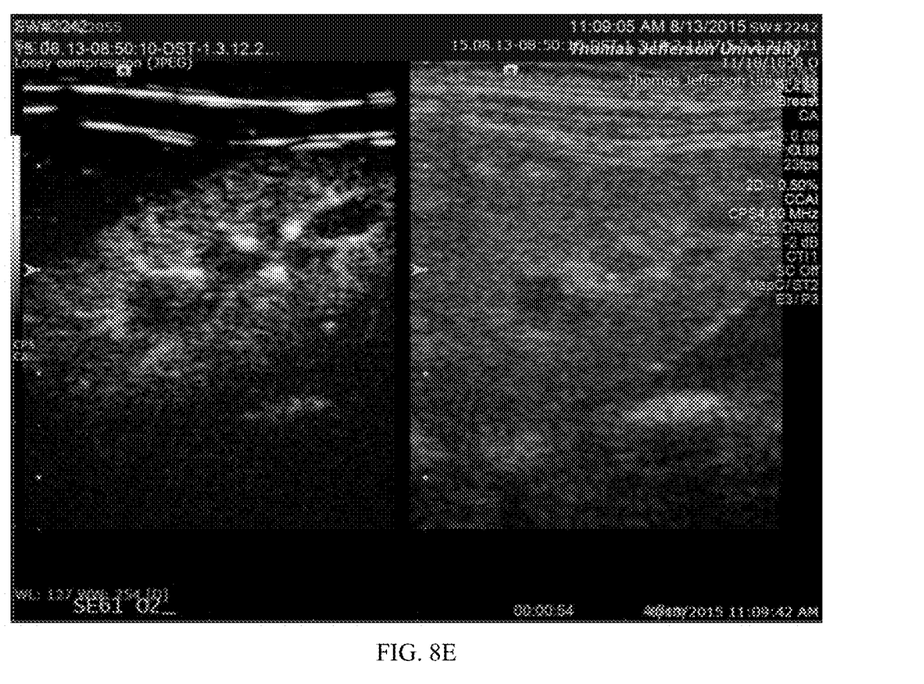

In vivo oxygen release immediately prior to therapy has demonstrated an ability to elevate hypoxic tumor oxygenation levels in animals (FIGS. 6 and 7). This is significant because a relatively small increase in oxygen partial pressure can result in significant sensitization. The relationship between $pO_2$ and radiosensitivity has been well studied in vitro: while cells at a $pO_2$ of <2 mmHg are almost completely radiation-insensitive, cell sensitivity reaches its asymptotic peak at approximately 30 mmHg. In one embodiment, the method of oxygen release described herein is used to improve the effectiveness of radiotherapy and chemotherapy against cancer. Such method comprises: preparing an oxygen-filled UCA; injecting the UCA into a cancer patient's body; directing ultrasound radiation to a specific location of the cancer patient's body with an intensity sufficient to rupture the UCA; and applying radiotherapy and/or chemotherapy. Thus, the oxygen inside the UCA will be released to the local cancer tissue, and help the effectiveness of radiotherapy and chemotherapy.

Alternatively, the oxygen-filled UCA can be used to improve the effectiveness of a therapeutic agent. The method comprises the steps of: preparing an oxygen-filled UCA; co-injecting the UCA with the therapeutic agent into the circulatory system of the subject; and directing ultrasound radiation to a location of interest with an intensity sufficient to rupture the drug-containing UCA.

In another embodiment, the gas delivery method described herein can be used to enhance wound healing and treat wounds and other conditions that are susceptible through treatment with hyperbaric medicine. Examples of such wounds include ulcers, diabetic ulcers, pressure sores, and the like.

Following the same mechanism of delivering oxygen to a subject's body, UCA can be used as a drug delivery carrier. The method of delivery comprises: preparing a drug-contained UCA; injecting the UCA into the circulatory system of the subject; monitoring the UCA reaching a specific location of interest; and directing ultrasound radiation to that location of interest with an intensity sufficient to rupture the UCA. Thus, the drug releases to the location of interest after the rupture. A single UCA can contain both a drug and oxygen. Alternatively, a mixture of drug-containing UCAs and oxygen-containing UCAs can be utilized, either in parallel or in series. Drug-containing UCAs and examples of drugs that can be incorporated in UCAs are described in U.S. Patent Application Publication Nos. 2004/0258760, 2004/0258761, 2008/0247957, 2008/0279783, and 2009/0196827.

WORKING EXAMPLES

The invention is further described in detail by reference to the following working examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Abbreviations Used $O_2$: Oxygen
$pO_2$: Partial pressure of oxygen
$SE61_{O2}$: Experimental oxygen microbubble consisting of a SPAN®60 and water soluble vitamin E shell
FE-DBD: Floating Electrode Dielectric Barrier Discharge
PTPBS: Plasma-Treated Phosphate-Buffered Saline
SE61: UCA composed of SPAN®60 & water-soluble vitamin E
ddH2O: Double-distilled Water
NAC: N-acetyl-cysteine
PBS: Phosphate-Buffered Saline
DBD: Dielectric Barrier Discharge Materials Surfactants Two non-ionic surfactants were used for preparing the microbubbles. SPAN®60 (sorbitan monostearate) (S7010, lot #010M0128) was purchased from Sigma Aldrich (St. Louis, Mo.) and used without further purification. United States National Formulary grade TPGS (batch#78971100) was bought from Eastman Chemical and used without further purification.

Other Chemicals

Octafluropropane (99% min) was purchased from American Gas Group (Toledo, Ohio) and used after passing through a sterile 0.22 μm filter (Nalgene, Rochester, N.Y.) in an aseptic (laminar flow) hood. Pure oxygen gas was purchased from Airgas USA, LLC. (Radnor, Pa.) and used after passing through a sterile 0.22 μm filter. Phosphate buffer saline (0.1M) was used as the buffer for preparing and testing the microbubbles after filtration using a 0.22 μm GV DURAPORE® membrane filter (lot # R6AN42605) purchased from Millipore. Sodium chloride, potassium chloride, sodium phosphate dibasic and potassium phosphate monobasic were all obtained from Sigma Aldrich (St. Louis, Mo.). D-glucose (lyoprotectant agent for freeze-drying the microbubbles) and Nile Red was also obtained from Sigma Aldrich (St. Louis, Mo.). For freeze-drying and UCA storage, 15 mL lyophilization vials were obtained from West Pharmaceutical Services (Lionville, Pa.).

Methods

Microbubble Fabrication

The UCA used in this study (termed $SE61_{O2}$) was prepared according to the method described in Solis et al., "Preserving Enhancement in Freeze-Dried Contrast Agent ST68: Examination of Excipients." Int. J. Pharm. 396:(1-2): 30-38 (2010). In summary, SPAN60® (sorbitan monostearate; 1.5 g) and water soluble vitamin E (d-alpha tocopheryl polyethylene glycol 1000 succinate) (TPGS; 1.3 g) were dissolved in 50 ml of phosphate buffered saline (PBS) and autoclaved for 30 minutes. The mixture was cooled under magnetic stirring and placed in an ice bath and continuously sonicated for 3 minutes at 110 W using a 0.5-inch probe horn (CL4 tapped horn probe with 0.5" tip, Misonix Inc., Farmingdale, N.Y.). The solution was purged with a steady stream of octafluoropropane before and during the sonication. Microbubbles were extracted from the solution via gravity separation in a 250 ml glass separation funnel, washed 3 times with cold (4° C.) PBS every 90-120 minutes using the same separation funnels. Two milliliter aliquots of native bubble suspension were pipetted with a pipet specifically designed for viscous fluids (GILSON® PIPETMAN®, Middleton, Wis.), into 15 ml lyophilization vials. Finally, 0.5 ml 400 mM glucose (Sigma Aldrich) was added to each vial as a lyoprotectant.

The 2.5 ml samples in lyophilization vials were freeze-dried. In brief, FLUORTEC® lyophilization stoppers were inserted into the vials to the first groove (leaving a gap for air to escape). The samples were flash-frozen in liquid nitrogen for 5 minutes and subsequently freeze-dried for 24 hours on a VIRTIS® Benchtop freeze-dryer (Gardiner, N.Y.) fitted with a two shelf assembly that had been previously cooled to −80° C. The conditions during this process were −76.5° C. (in the vacuum drier chamber) and 17-20 μBar. Before removing the samples, the piston was lowered to depress the stoppers, effectively vacuum sealing the vials. The gas of choice (nitrogen or oxygen, Airgas LLC, Radnor, Pa.) was introduced through the FLUORTEC® stoppers using a sterile syringe needle, after passage through a sterile 0.22 μm NALGENE® filter (Nalge Nunc International, Rochester, N.Y.) at an initial flow rate of 50 ml/min for 5-10 seconds then 20 ml/minutes for one minute to insure the vials were filled. The procedure was performed under an aseptic laminar flow hood and vials sealed with parafilm until use. Immediately prior to use, the vials were charged with 2 ml of deionized water. In certain embodiments, the deionized water will be saturated with oxygen. As a control group (to ensure all ultrasound enhancement is attributed to the addition of $O_2$), samples were maintained under vacuum and reconstituted in the usual way with deionized water prior to use (thereby creating bubbles without additional gas).

Particle Morphology, Size, and Concentration Characterization

Particle morphology was assessed by light microscopy using an OLYMPUS® IX71 microscope (Tokyo, Japan) at 40× magnification. The size distribution of the microbubbles was analyzed using a ZETASIZER® Nano ZS (Malvern Instruments, Worcestershire, UK) in Z-average mode, using dynamic light scattering techniques. Using this technique, a 50 μl sample was dispersed in 950 μl PBS in tapered cuvettes for size-analysis. Particle counting was performed using a flow cytometer, LSRII (BD Biosciences, San Jose, Calif.). With this technique, 10 μl of microbubbles were added to 0.5 ml of deionized water and 10 μl of UV COUNTBRIGHT® Absolute Counting Beads (containing 9,800 beads used as a counting standard; Life Technologies, Grand Island, N.Y.). Counting beads and $SE61_{O2}$ particles were separated using FSC-A and PE-A filters.

UCA Stability and Ultrasound Enhancement Characterization

A custom-built acrylic plastic sample holder with a clear acoustic window (2.5 cm×2.5 cm) was placed in a tank filled with 75 liters of deionized water (temperature-controlled to 37° C.) for in vitro acoustic testing of the UCA. A single element 5 MHz transducer (Panametrics, Waltham, Mass.; 12.7 mm diameter, −6 dB bandwidth of 91% and focal length of 50.8 mm) was focused through the acoustic window using an x-y positioning system (Edmund Scientific, Barrington, N.J.) and a 5072 pulser-receiver (Panametrics) was used to generate acoustic pressures of 0.69 MPa peak negative pressure with a pulse repetition frequency of 100 Hz. This ultrasound signal is expected to be strong enough to detect microbubble response, but not expected to generate inertial cavitation. A magnetic stir bar constantly recirculated the bubbles through the focus of the transducer. Reflected signals from the UCA were detected by the same transducer and amplified 40 dB before being read by a digital oscilloscope (LECROY® 9350A, LeCroy Corporation, Chestnut Ridge, N.Y.). Data acquisition and processing was done on a computer with LABVIEW® 7.1 (National Instruments, Austin, Tex.).

To determine the dose dependence of ultrasound signal enhancement, a cumulative dosage response curve was generated for UCA dosages of 0 to 1080 μl/l (0 to 7 E7 microbubbles/l) and ultrasound enhancement expressed in dB relative to the baseline (0 μl/l). To measure microbubble stability in the ultrasound beam, 280 μl/l (1.8 E7 microbubbles/l) of UCA were added to the sample container and enhancement measured once per minute over 15 minutes. Ultrasound enhancement at each time point was then normalized to the initial signal enhancement. The ability to detect the UCA using a commercial ultrasound scanner was also investigated using a LOGIQ® 9 ultrasound scanner with 9L probe operating in nonlinear contrast imaging mode (GE Healthcare, Milwaukee, Wis.). A bolus injection of 1 ml/l of UCA was circulated through a flow phantom (model 524; ATS Laboratories, Bridgeport, Conn.) with a 6-mm-diameter vessel embedded at a depth of 2 cm in urethane rubber using a roller pump set at 250 ml/min. Ultrasound images were then obtained every minute for 15 minutes.

Determination of Release Kinetics after Ultrasound Triggering

Oxygen release kinetics were measured using an OXYLITE® 2000 with bare fiber $pO_2$ probe (Oxford Optronix, Oxford, United Kingdom). Ultrasound triggering was performed using a SonixRP scanner with a PA4-2 cardiac probe operating at 100% acoustic output (approximately 3.6 MPa peak-peak pressure) at 4 MHz in power Doppler mode. Two milliliters of reconstituted agent was added to 100 ml of degassed saline. Samples were triggered with ultrasound over 20 minutes with readings obtained every 30 seconds. The experimental group consisted of 2 ml of $O_2$ filled $SE61_{O2}$ combined with ultrasound, while control groups consisted of 2 ml of $O_2$ filled $SE61_{O2}$ without ultrasound, 2 ml of nitrogen filled SE61 combined with ultrasound, and 2 ml of deionized water with ultrasound. All $pO_2$ values were normalized to baseline levels and expressed as change in mmHg.

Statistical Analysis

All experiments were repeated in triplicate from 3 independent samples and averaged. Statistical significance between groups was determined using a one-way ANOVA with a Bonferroni multiple comparison posttest. All statistics were performed in GRAPHPAD® Prism (Version 5.0, GraphPad Software, San Diego, Calif.) with significance determined by $\alpha=0.05$.

Results

Size, Stability, and Ultrasound Enhancement

Figure 1A:
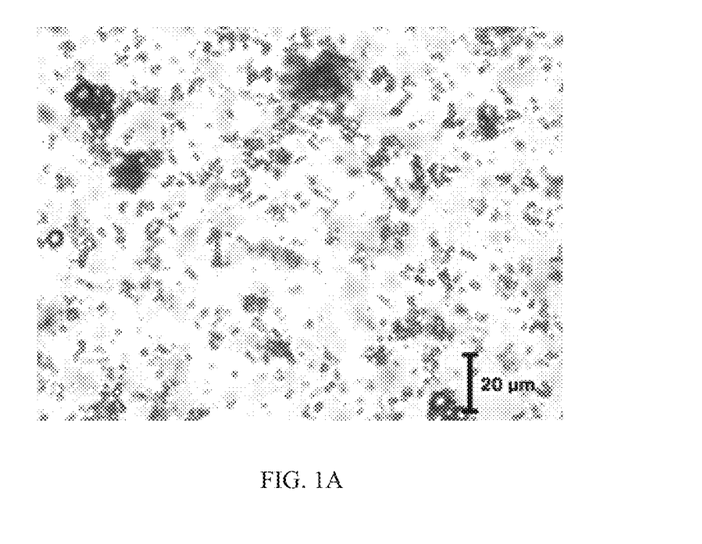
FIG. 1A is a light microscopy image of $SE61_{O2}$ at 40× magnification (size bar=20 μm).
Figure 1B:
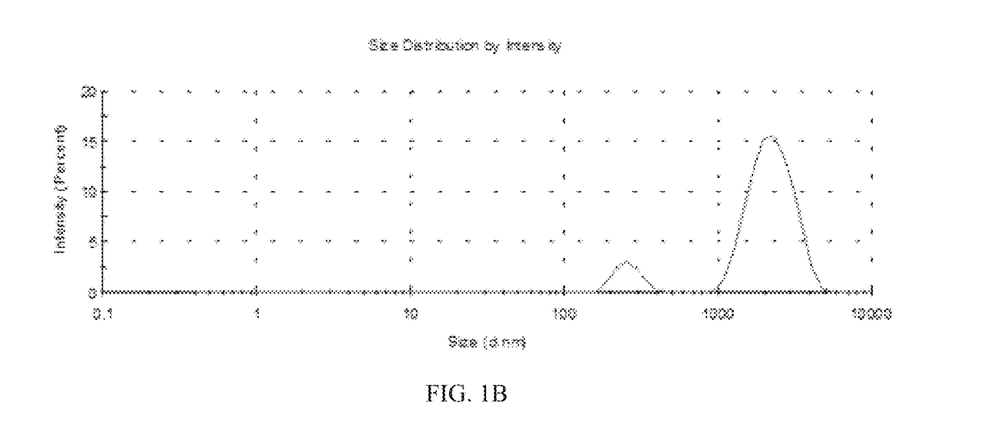
FIG. 1B depicts size distribution measurement of $SE61_{O2}$ by dynamic light scattering, showing a mean particle diameter of approximately 3 μm.
Figure 1C:
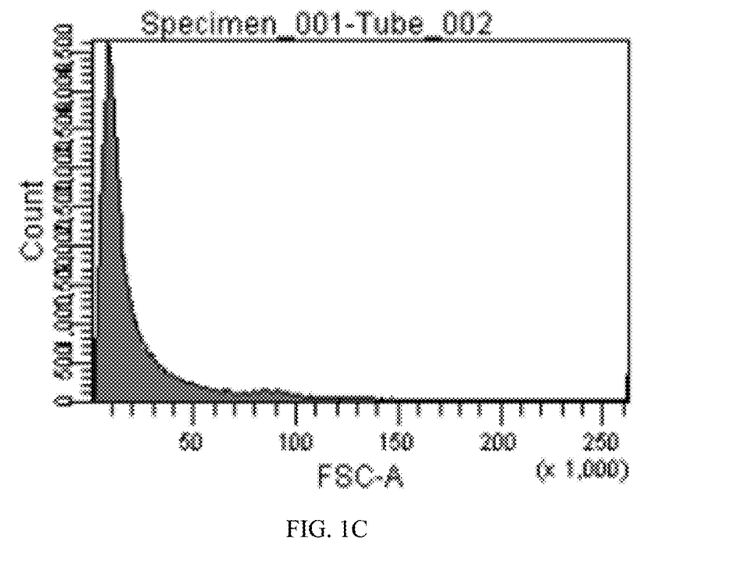
FIG. 1C depicts flow cytometry results for distinct, separate bubbles (black). Forward scattered light (FSC-A) is represented on the x-axis and particle counts on the y-axis. Populations were observed with a total bubble population of approximately $6.5 \times 10^7$ microbubbles/ml.
Figure 1D:
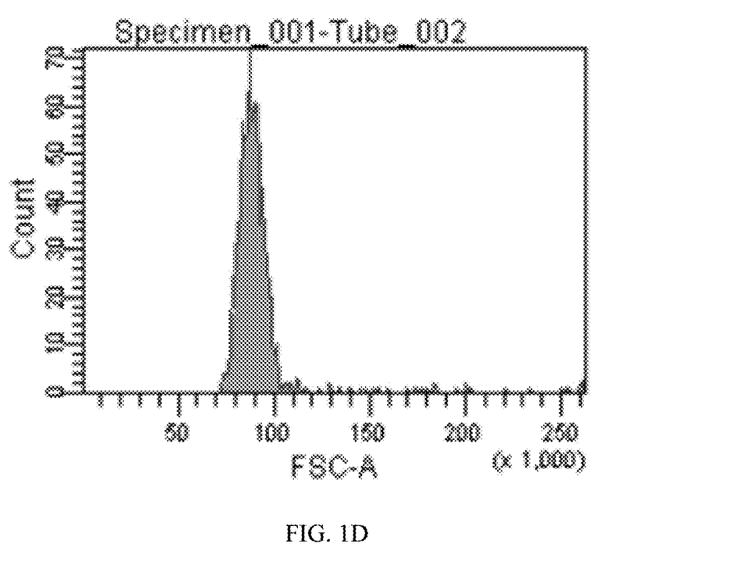
FIG. 1D depicts flow cytometry results for counting bead (red). Forward scattered light (FSC-A) is represented on the x-axis and particle counts on the y-axis. Populations were observed with a total bubble population of approximately $6.5 \times 10^7$ microbubbles/ml.

The $SE61_{O2}$ microbubbles were successfully charged with $O_2$ and remained intact when reconstituted with deionized water. Reconstituted particles demonstrated a spherical shape and smooth morphology on light microscopy as shown in FIG. 1A. These results demonstrate the presence of microbubbles after reconstitution. Analysis of the particle size distribution by dynamic light scattering (FIG. 1B) showed an average diameter of 3.1±0.1 μm with a polydispersity index of 0.89±0.18 indicating a broad size distribution. Particle counting by flow cytometry (example plot shown in FIG. 1C and FIG. 1D) showed the $SE61_{O2}$ microbubbles consisted of approximately $6.5\pm0.8\times10^7$ microbubbles/ml after suspension in 2 ml of saline.

Figure 2A:
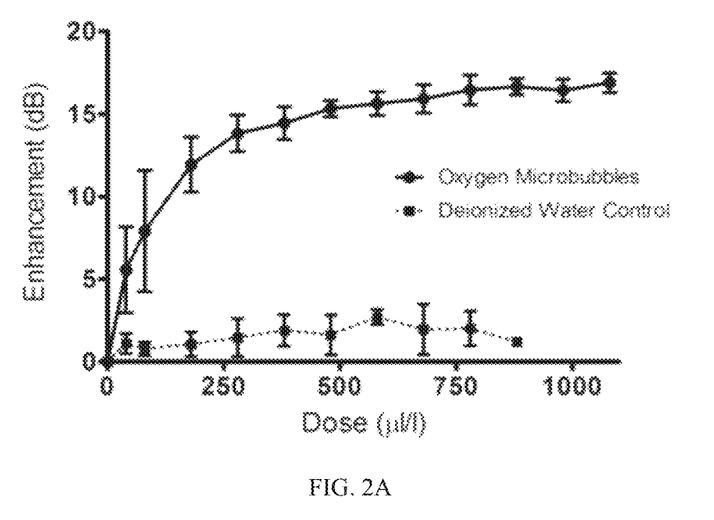
FIG. 2A depicts in vitro ultrasound enhancement of $SE61_{O2}$ and the controlled microbubbles (control).
Figure 2B:
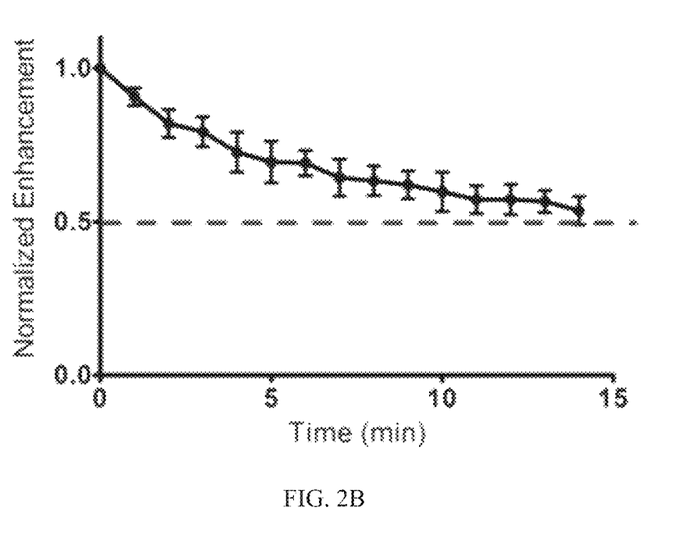
FIG. 2B depicts that oxygen-filled microbubbles also showed good overall stability with a half-life of over 15 minutes (half-life threshold displayed by dashed line).
Figure 3:
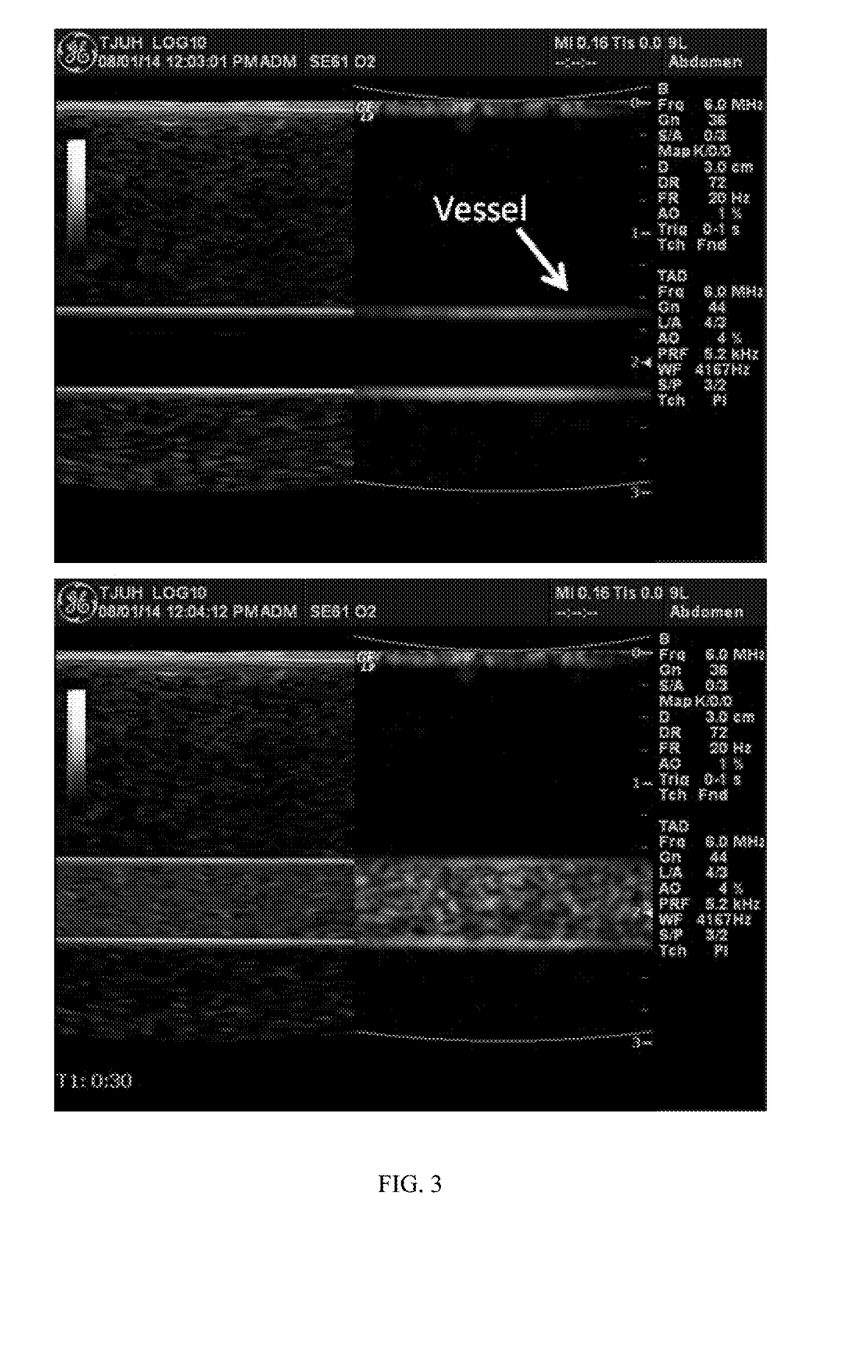
FIG. 3 depicts in vitro ultrasound enhancement of $SE61_{O2}$ in a flow phantom using a commercial ultrasound scanner at baseline (top) and 30 seconds post injection (bottom).

Results of ultrasound enhancement and stability testing are shown in FIG. 2. In vitro enhancement at 5 MHz (FIG. 2 left) increased with $SE61_{O2}$ dose, with a peak enhancement of 16.9±1.0 dB at a dose of 880 μl/l (5.7 E7 microbubbles/l). As a control, freeze-dried SE61 was reconstituted with deionized water alone (no gas), to detect the presence of any remaining octafluoropropane. No detectable enhancement was observed (FIG. 2 left) with enhancement levels remaining at baseline levels (average enhancement 1.4±0.9 dB, p<0.0001 relative to $SE61_{O2}$). The $SE61_{O2}$ bubbles were insonated at low level ultrasound (0.69 MPa) to determine microbubble stability (FIG. 2 right). These microbubbles demonstrated good overall stability, with a half-life over 15 minutes. Finally, 880 μl/l of $SE61_{O2}$ microbubbles were imaged in a flow phantom using a commercial scanner (FIG. 3). The agent demonstrated substantial enhancement within the 6 mm vessel lumen at a depth of 2 cm after injection (bottom), relative to baseline (top) in both grayscale B-mode ultrasound (left split screen), and nonlinear contrast mode (right split screen, in gold).

In Vitro Oxygen Release

Oxygen release experiments were performed to determine the ability of $SE61_{O2}$ to locally increase $O_2$ concentrations when triggered with ultrasound (FIG. 4). All groups showed a gradual rise in partial pressure of $O_2$ ($pO_2$) due to gas exchange between the degassed saline and atmospheric air (average of 40 mmHg over 20 mins). However, $pO_2$ levels were found to be significantly elevated over a 20 minute period when $SE61_{O2}$ bubbles were insonated relative to ultrasound alone, uninsonated $SE61_{O2}$, and insonated nitrogen filled SE61 ($p<0.001$). This difference became apparent after 1 minute of insonation (with differences of 12.0, 11.4, and 7.7 mmHg respectively) and remained consistent throughout the full 20 minutes (23.0, 13.8, and 20.6 mmHg respectively at 20 minutes). Untriggered $SE61_{O2}$ showed higher $pO_2$ levels at 20 minutes relative to triggered nitrogen filled SE61 (6.8 mmHg), although their release curves were not found to be significantly different ($p=0.5$).

In Vivo Results

Preliminary in vivo results demonstrate the ability of the UCA to temporarily elevate hypoxic tumor oxygenation levels in mice (FIGS. 6 and 7). While imaging was not optimized for destruction of SE61 and tumor oxygenation appeared to be very dependent on $pO_2$ probe positioning, triggering of $SE61_{O2}$ showed an increase in tumor oxygenation levels in both animals.

FIG. 6 shows example ultrasound images and tumor oxygenation levels over time in both animals. The top ultrasound image of FIG. 6 shows the triggering sequence of contrast arrival within the periphery of the tumor with slight peripheral enhancement denoted with two arrows. The middle ultrasound image shows the flash-destructive ultrasound pulse used to destroy the microbubbles, and the bottom ultrasound image shows a slight decrease in peripheral enhancement immediately after microbubble destruction. The $pO_2$ probe introduced into the tumor through the catheter was observed in all images (arrow in the bottom ultrasound image). Both animals showed an increase in $pO_2$ during triggering of $SE61_{O2}$, although measurements appeared to be highly dependent on probe position (FIG. 7). Ultrasound triggering in mouse 1 showed an increase of 27.4 mmHg, with elevated tumor oxygen levels lasting 1.7 min after injection before returning to baseline. $SE61_{O2}$ triggering in mouse 2 resulted in a 30.4 mmHg increase, with elevated tumor oxygen levels lasting over 4 min. Ultrasound-triggering of $SE61_{N2}$ resulted in no discernible increase in oxygen partial pressure in either mouse. Untriggered $SE61_{O2}$ (i.e., without ultrasound exposure) resulted in no increase in oxygen partial pressure in one animal, and a brief (20 s) 5.6 mmHg increase in the second animal.

Referring now to FIGS. 8A-8E, in vivo imaging in a 3 kg swine after injection of SE61 filled with $O_2$ demonstrated the enhancement of the renal vasculature. Imaging was performed using a SIEMENS® 53000 ultrasound system with 9 MHz linear probe in CPS mode. Microbubble signal is displayed in gold (left half of images), while the normal B-mode ultrasound is displayed in grayscale (right half of images). FIGS. 8A, 8B, 8C, 8D, and 8E were taken at 19, 26, 34, 44, and 54 seconds after injection, respectively. The peak enhancement occurred at 44-54 seconds post injection (FIGS. 8D and 8E) and lasted up to 3 minutes. These data demonstrate the stability of the oxygen filled microbubble and ability to deliver oxygen in a large animal model.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. An ultrasound contrast agent (UCA) comprising:
an outer shell, and
a gas core,
wherein said gas core is filled with between 98% and 100% pure oxygen without a perfluorocarbon, and
wherein said outer shell comprises:
a first surfactant, and
a second surfactant,
wherein the first surfactant comprises d-α-tocopheryl polyethylene glycol 1000 succinate (TPGS),
wherein the UCA induces a statistically significant increase in oxygen concentration when in solution and insonated relative to in solution without insonation, and
wherein the insonated UCA has a half-life under 5 MHz ultrasound of from about 5 minutes to about 20 minutes.

2. The UCA of claim 1, wherein the second surfactant is selected from the group consisting of: sorbitan esters, alkylphenol ethoxylate-based surfactants, alcohol ethoxylate-based surfactants, silicone-based surfactants, alkyl polyethylene oxide), alkylphenol poly(ethylene oxide), copolymers of polyethylene oxide) and polypropylene oxide), alkyl polyglucosides, fatty alcohols, cocamide MEA, cocamide DEA, and polysorbates.

3. The UCA of claim 1, wherein the mean diameter of the UCA is in the range of 1 μm to 10 μm.

4. The UCA of claim 1, wherein the mean diameter of the UCA is in the range of 2 μm to 7 μm.

5. The UCA of claim 1, wherein the mean diameter of the UCA is about 3 μm.

6. The UCA of claim 1, wherein the half-life of the UCA under 5 MHz ultrasound is in the range of 10 to 20 minutes.

7. The UCA of claim 1, wherein the half-life of the UCA under 5 MHz ultrasound is about 15 minutes.

8. The UCA of claim 1, wherein:
the second surfactant is sorbitan monostearate.

9. The UCA of claim 8, wherein the mean diameter of the UCA is about 3 μm.

10. A method of delivering oxygen to a local area of a subject's body, comprising
a. injecting a composition comprising a UCA of claim 1 into the subject's body; and
b. directing ultrasound radiation to the local area in an intensity sufficient to rupture the UCA.

11. A method of improving effectiveness of radiotherapy and chemotherapy against cancer, comprising the steps of:
a. injecting a composition comprising a UCA of claim 1 into a subject suffering from cancer;

b. directing ultrasound radiation to a location of said cancer in an intensity sufficient to rupture the UCA; and c. applying radiotherapy and/or chemotherapy.

12. The UCA of claim 1, wherein the UCA is stable long enough to pass through a circulatory system of a large animal.

\* \* \* \* \*